United States Patent
Congy et al.

(10) Patent No.: US 10,405,816 B2
(45) Date of Patent: Sep. 10, 2019

(54) COLLIMATOR FOR CEPHALOMETRIC EXTRA ORAL DENTAL IMAGING DEVICES

(71) Applicant: Trophy, Croissy-Beaubourg (FR)

(72) Inventors: Philippe Congy, Croissy-Beaubourg (FR); Olivier Martino, Croissy-Beaubourg (FR)

(73) Assignee: TROPHY, Croissy-Beaubourg (FR)

( * ) Notice: Subject to any disclaimer, the term of this patent is extended or adjusted under 35 U.S.C. 154(b) by 213 days.

(21) Appl. No.: 15/523,498

(22) PCT Filed: Jan. 14, 2015

(86) PCT No.: PCT/IB2015/000346
§ 371 (c)(1),
(2) Date: May 1, 2017

(87) PCT Pub. No.: WO2016/087912
PCT Pub. Date: Jun. 9, 2016

(65) Prior Publication Data
US 2017/0311909 A1  Nov. 2, 2017

Related U.S. Application Data

(60) Provisional application No. 62/087,352, filed on Dec. 4, 2014.

(51) Int. Cl.
*A61B 6/04* (2006.01)
*A61B 6/06* (2006.01)
*A61B 6/14* (2006.01)
*G21K 1/02* (2006.01)

(52) U.S. Cl.
CPC .............. *A61B 6/14* (2013.01); *A61B 6/04* (2013.01); *A61B 6/06* (2013.01); *G21K 1/02* (2013.01)

(58) Field of Classification Search
CPC .... A61B 6/04; A61B 6/06; A61B 6/14; G21K 1/02
See application file for complete search history.

(56) References Cited

U.S. PATENT DOCUMENTS

| 5,511,106 A * | 4/1996 | Doebert | A61B 6/032 378/146 |
| 2012/0243662 A1 * | 9/2012 | Loustauneau | A61B 6/06 378/63 |

(Continued)

FOREIGN PATENT DOCUMENTS

| DE | 3930022 A1 | 3/1990 |
| FR | 2953707 A1 | 6/2011 |
| WO | 2008/113715 A1 | 9/2008 |

OTHER PUBLICATIONS

International Search Report, International application No. PCT/IB2015/000346, dated Jul. 29, 2015, 2 pages.

*Primary Examiner* — Chih-Cheng Kao (57) ABSTRACT

An integral collimator for an extra-oral imaging system that includes a lead plate surrounding an elongated fixed slot aperture and includes a unitary body in substantially continuous contact with an outer surface of the elongated lead plate. The unitary body can include a lower portion surrounding the elongated lead plate and an upper portion, where the upper portion includes a protrusion configured to engage a transport mechanism for translation in a direction orthogonal to a path of the x-ray.

12 Claims, 5 Drawing Sheets

(56) References Cited

U.S. PATENT DOCUMENTS

2013/0307923 A1\* 11/2013 Inglese .................. A61B 6/025
                                                                    348/36
2015/0297158 A1\* 10/2015 Bothorel .................. A61B 6/06
                                                                    378/20

\* cited by examiner

COLLIMATOR FOR CEPHALOMETRIC EXTRA ORAL DENTAL IMAGING DEVICES

CROSS REFERENCE TO RELATED APPLICATIONS

This application claims the benefit of and is a U.S. National Phase filing of PCT Application PCT/IB15/00346 filed Jan. 14, 2015, entitled "COLLIMATOR FOR CEPHALOMETRIC EXTRA ORAL DENTAL IMAGING DEVICES", in the name of Congy et al., which claims the benefit of U.S. Provisional application U.S. Ser. No. 62/087,352, provisionally filed on Dec. 4, 2014 entitled "COLLIMATOR FOR CEPHALOMETRIC EXTRA ORAL DENTAL IMAGING DEVICES", in the names of Congy et al., all of which are incorporated herein by reference in their entirety.

FIELD OF THE INVENTION

The invention relates generally to the field of dental x-ray imaging, and more particularly, to imaging in a cephalometric x-ray mode for dental applications. Further, the invention relates to a combined cephalometric, panoramic and computed tomography dental imaging apparatus and/or methods.

BACKGROUND

In the dental imaging field, a cephalometric imaging device includes an x-ray source that emits a conical or pyramidal shaped x-ray beam towards a cephalometric imaging sensor mounted at the end of a long arm. A patient's positioning unit to position the patient's head is located between the x-ray source and the cephalometric sensor at the vicinity of the cephalometric sensor. Then, the x-ray beam originating from the remote x-ray source radiates the patient's skull before impinging the cephalometric sensor. The digitalization of the signal and the treatment of the data lead to the reconstruction of a projection image of the skull or at least a part of the skull of the patient.

In a general dental cephalometric imaging device, a distance between the x-ray source and the cephalometric sensor is typically 1.7 m. As the patient's positioning unit located at the vicinity of the cephalometric sensor and away from the x-ray source, the magnitude ratio of the image size to the patient's skull size is close to 1 for any part of the skull. In particular in profile imaging, a first half of the skull is closer to the sensor than the other half. Thanks to the small ratio of the source-sensor distance to the source-patient distance, the magnitude factor for the projection of both halves of the skull on the cephalometric sensor along the conical x-ray beam is almost the same and distortion of the image is then reduced or avoided.

The cephalometric sensor can have the shape of a thin vertical cylinder with a large (e.g., typically 30) height-to-width ratio. A collimator having the same shape as the cephalometric sensor is used to collimate the x-ray beam originating from the remote x-ray source. This collimator is positioned in front of the patient's positioning unit and in coincidence with the cephalometric sensor so that the x-ray beam is shaped before radiating the patient. The cephalometric imaging process includes accumulating frames of data from the cephalometric sensor while the cephalometric sensor is translated from one side of the skull to the other side (e.g., horizontally, vertically) with a combined and coordinated movement of the collimator. The frames of data are then merged and treated to reconstruct a projection image of the whole skull. In the cephalometric or skull imaging technique, the patient can be positioned facing the x-ray beam or in a profile position.

The collimator according to the prior art is usually made of a plurality of metallic plates assembled in a complicated way, the ensemble being covered by a plastic cover. This makes the prior art collimator complicated and expensive to manufacture. Further, the link between the metallic parts and the plastic cover has to be precisely engineered to avoid any break between each part.

There is still a need for a cephalometric collimator that is easy and/or cheap to manufacture.

SUMMARY

An aspect of this application is to advance the art of medical digital radiography, particularly for dental applications.

Another aspect of this application is to address, in whole or in part, at least the foregoing and other deficiencies in the related art.

It is another aspect of this application to provide, in whole or in part, at least the advantages described herein.

An advantage offered by apparatus and/or method embodiments of the application relates to improved imaging of teeth, jaw and head features surfaces at a lower cost over conventional imaging methods.

An advantage offered by apparatus and/or method embodiments of the application relates to providing a unitary body collimator for a dental cephalometric imaging apparatus.

An advantage offered by apparatus and/or method embodiments of the application relates to providing a continuous contact between a first metal member, which includes a slit and a protective layer to reduce or eliminate mechanical stress therebetween in a collimator for a dental cephalometric imaging apparatus.

An advantage offered by apparatus and/or method embodiments of the application relates to providing a unitary collimator for a dental cephalometric imaging apparatus that includes a molded protective layer over all exterior sides of a metal plate, where the molded protective layer includes an elongated engagement projection for coupling to a transport mechanism and the metal plate includes an elongated slit therethough.

According to one aspect of the disclosure, there is provided a method for manufacturing a collimator for a cephalometric imaging device that can include forming an elongated metallic plate surrounding a fixed aperture; overmolding a unitary body on the elongated metallic plate at least partially filling the fixed aperture; and milling a slot in the unitary body in coincidence with the fixed aperture.

According to one aspect of the disclosure, there is provided an extra-oral imaging system, the extra-oral system that can include a support base adjustable in at least one dimension; a cephalometric module coupled to the support base and configured to position a cephalometric imaging sensor about a first imaging area formed with an x-ray source, where x-rays from the x-ray source impinge the cephalometric sensor after radiating the first imaging area; a cephalometric patient positioning unit positioned operatively near the first imaging area; and an integral cephalometric collimator comprising an elongated metallic plate surrounding a fixed slot aperture and encased on at least a portion of all exterior sides by a unitary body in substantially continuous contact with an outer surface of the elongated metallic plate.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

DESCRIPTION OF EXEMPLARY EMBODIMENTS

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

Figure 1:
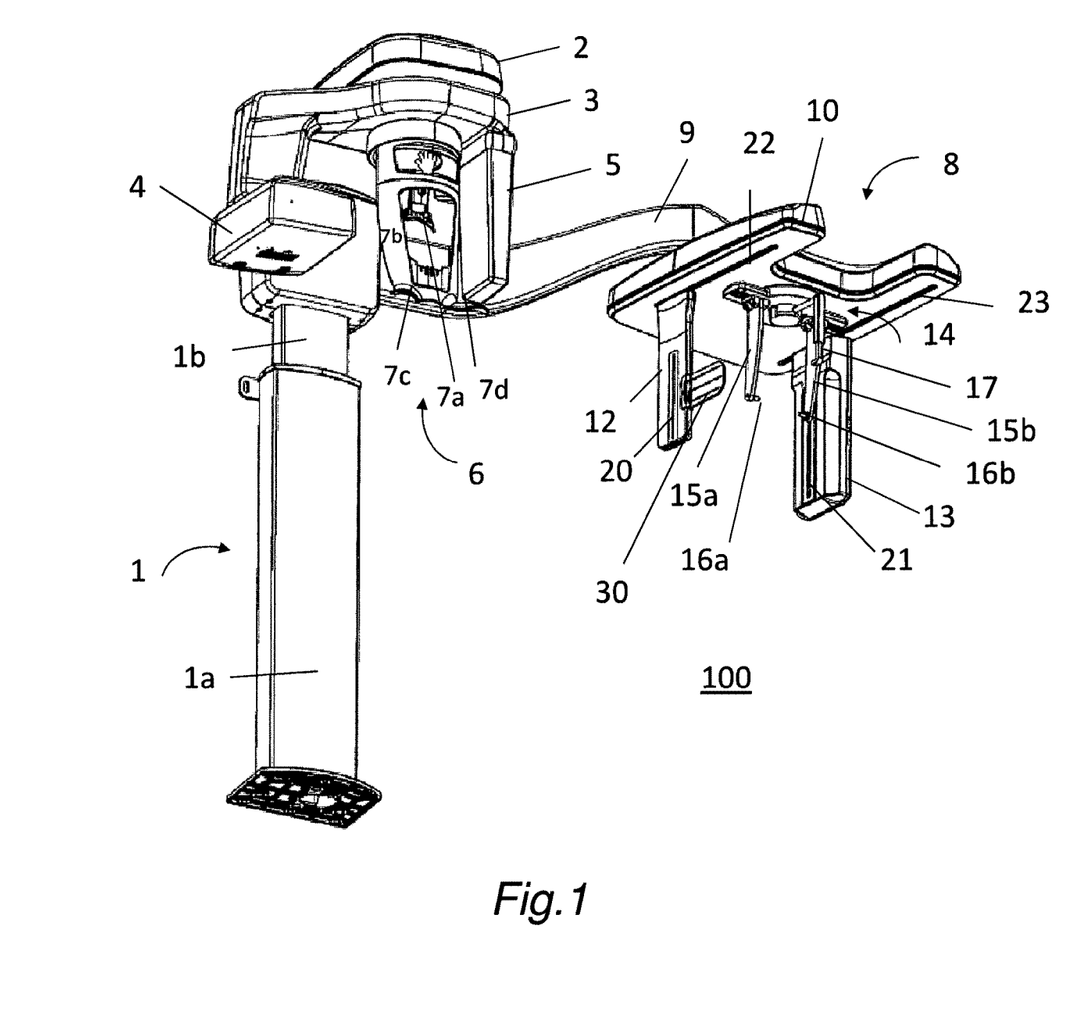
FIG. 1 is a diagram that shows a perspective view of a related art extra-oral dental imaging system including a cephalometric imaging unit.

FIG. 1 is a diagram that shows a perspective view of a related art extra-oral dental imaging system including a cephalometric imaging unit. As shown in FIG. 1, an exemplary extra-oral dental imaging system 100 includes a support structure that can include a support column 1. The column 1 may be adjustable in two-dimensions or three-dimensions. For example, the column 1 can be telescopic and may include an upper part 1b sliding inside a lower part 1a. A horizontal mount 2 may be supported or held by the vertical column 1 and can support a rotatable gantry 3. An x-ray source 4 and a first x-ray imaging sensor 5 are attached or coupled to the gantry 3 in correspondence (e.g., opposite, aligned) to each other. The first x-ray sensor 5 may be a panoramic (e.g., slit-shaped) sensor or a Computerized Tomography (e.g., rectangular, square-shaped) sensor. Preferably, the x-ray beam originating from the x-ray source 4 impinges the sensor 5 after radiating a first imaging area or the patient. A first patient positioning and holding system 6 can be operatively positioned near or in the first imaging area. For example, the first patient positioning and holding system 6 may be between the x-ray source 4 and the first x-ray imaging sensor 5. The first patient positioning and holding system 6 can include a forehead support 7a and a shield 7b including two handles 7c and 7d. The patient can then grasp the handles 7c and 7d and remain motionless during the CT scan or panoramic scan.

More remote from the x-ray source 4, a cephalometric imaging unit 8 may be held in correspondence to the x-ray source 4. For example, as shown in FIG. 1, the cephalometric imaging unit 8 can be attached or coupled to the upper part 1b of the vertical column via an extended (e.g., horizontal) cephalometric arm 9. The cephalometric imaging unit 8 can include a mount 10 supporting a collimator 12, a second or cephalometric sensor 13 and a second patient positioning and holding system 14. As can also be seen in FIG. 2, the second patient positioning and holding system 14 can include a forehead support 17 and two temporal holding members 15a and 15b each supporting an ear rod 16a and 16b. Preferably, the x-ray beam originating from the x-ray source 4 impinges the sensor 13 after radiating a second or cephalometric imaging area or the patient. The second patient positioning and holding system 14 can be operatively positioned near or in the second imaging area. For example, thanks to the second patient positioning and holding system 14, the patient is precisely and repeatedly positioned between the collimator 12 and the sensor 13, preferably in the second imaging area. One or more of the holding members 15a and 15b can respectively slide along rails 15ar and 15br so that the distance between the two ear rods 16a and 16b can be changed to fit the patient's head. The forehead support 17 can also be adjustable. For example, the forehead support 17 can be adjustable in at least two orthogonal dimensions by sliding along the horizontal and vertical directions. Alternatively, the forehead support 17 can be adjustable in three-dimensions or around three or more orthogonal axis.

Figure 2:
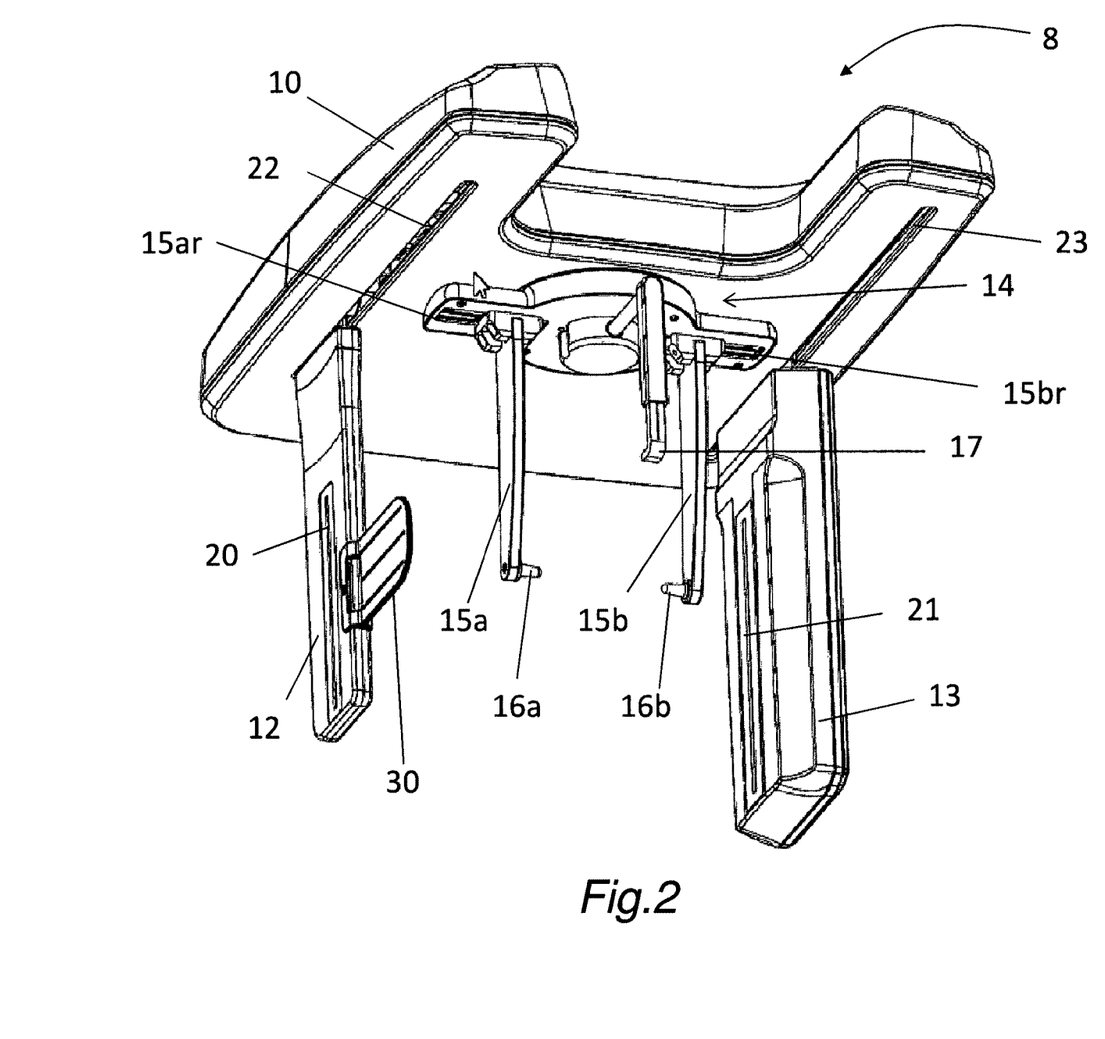
FIG. 2 is a diagram that shows a perspective view of a cephalometric imaging unit of FIG. 1.

As shown in FIG. 2, the collimator 12 can include an elongated opening or slit 20 to shape an x-ray beam. The x-ray sensor 13 can include an active area 21 having an elongated shape (e.g., a vertical slit) facing the vertical slit 20 of the collimator 12 (e.g., across the second imaging area). The sensor 13 and the collimator 12 face each other so that the sensor 13 can receive the x-rays originating from the x-ray source 4 after the x-ray beam was shaped by the collimator 12 and after the x-ray beam radiated the patient positioned and held on the second patient's positioning and holding system 14. For the scanning of the complete skull of the patient, both the collimator 12 can move or slide during the x-ray scan along a rail 22 and the sensor 13 can move or slide along the rail 23. Both rails 22, 23 can be coupled to the mount 10. For example, the rails 22, 23 can be embodied on a lower face of the mount 10 of the cephalometric imaging unit 8. At any time during the cephalometric x-ray scan, an alignment may exist between a primary collimator in front of the source (not shown), the slit 20 of the collimator 12 and the active area of the sensor 13. Such x-ray alignment is disclosed, for example, in U.S. Pat. No. 5,511, 106. At selected positions of the ensemble during the cephalometric scan, an x-ray digital image is obtained by the sensor 13. At the end of the cephalometric scan, an image reconstructing device (e.g., hardware, software and/or image processing) reconstructs the whole skull image on the basis of the plurality of images obtained during the cephalometric scan, for example using algorithms known to the person skilled in the art.

For a correct patient's positioning allowing a good image quality in the exemplary extra-oral dental imaging system 100, the Frankfort plane containing a straight line passing though the bottom of the eye socket and the ear canal must be horizontal. For the purpose of controlling that the Frankfort plane is horizontal, an at least partially transparent visual indicator 30 can be used.

Figure 3:
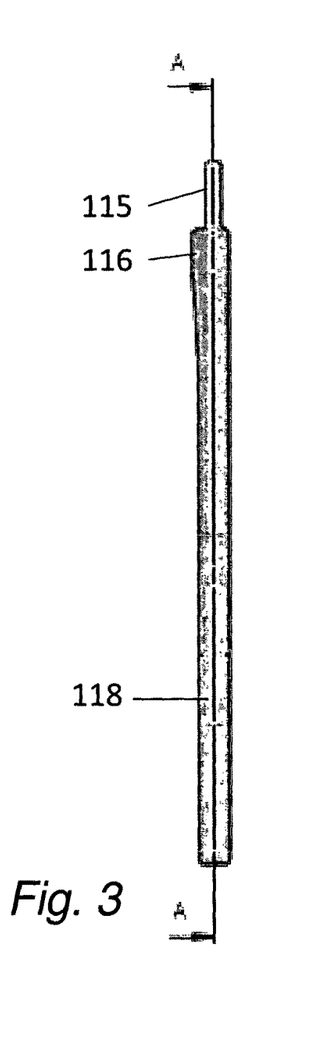
FIG. 3 is a diagram that shows a side view of an exemplary collimator embodiment of a cephalometric imaging unit according to the application.
Figure 4:
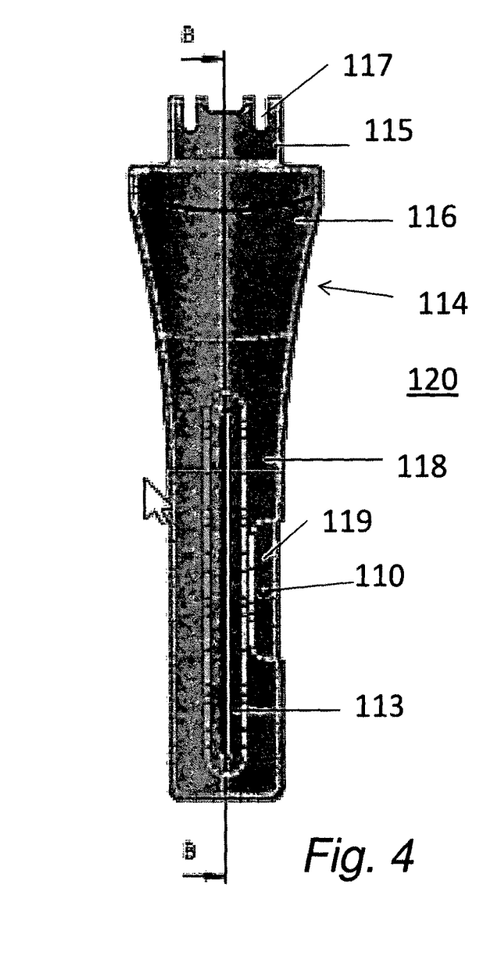
FIG. 4 is a diagram that shows a front view of an exemplary collimator embodiment of a cephalometric imaging unit according to the application.

FIG. 3 is a diagram that shows a side view of an exemplary collimator embodiment of a cephalometric imaging unit according to the application. FIG. 4 is a diagram that shows a front view of an exemplary collimator embodiment of a cephalometric imaging unit according to the application. As shown in FIGS. 3-4, an exemplary collimator can be used in the related art extra-oral dental imaging system shown in FIG. 1.

As shown in FIG. 3, a collimator 120 can include a lead plate 112 overmolded with a unitary body 114. In one embodiment, the body 114 can be made of a mix of polyester resin and glass fiber. One such material is known under the name Fiber Reinforced Plastic or FRP. This material is preferred has it offers good mechanical properties, a good resistance against corrosion, is light weight and is possible to mold. A third material or additional materials can also be added to the composition of the body 114 so long as the selected characteristics (e.g., good mechanical properties, a good resistance against corrosion, light weight and/or moldable) substantially unchanged, or at least not substantially negatively impacted.

In certain exemplary embodiments, the lead plate 112 can have a thickness comprised between 0.5 mm and 4 mm, preferably between 1 mm and 3 mm, and more preferably, the thickness is equal to 2 mm. Lead is well known in the art of collimators for its ability to absorb X-rays. A slot 113 can be formed in the front face of the lead plate 112 to allow the passage of the X-ray beam and to shape the x-ray beam into a thin fan beam. In one embodiment, the slot 113 can be formed in the middle of the front face of the collimator 120. In certain exemplary embodiments, the thickness of the slot 113 can be comprised between 2 mm and 8 mm, preferably between 3 mm and 6 mm, and more preferably, equal to 4.5 mm. The length of the slot 113 can be equal to 200 mm. the length-to-width ration of the slot 113 can be bigger than 30. Typically, the slot 113 is slightly narrower than the thickness of the active area of the cephalometric sensor (e.g., sensor 13) positioned on the other side of a patient's positioning module (e.g., system 14).

The lead plate 112 can be covered by the body 114 made of FRP material. In certain exemplary embodiments, first the whole lead plate 112 is preferably covered by the overmolded body 114, namely the four sides (e.g., left, right, top and bottom) and the front and rear sides are covered. Accordingly, the slot 113 of the lead plate can be filled with the FPR material. Then, a slot (e.g., slot 113) the same width as the slot 113 in the lead plate 112 can be milled out with a milling tool from the body 114.

The over molded body 114 can include a protrusion 115 with at least one or a plurality of notches 117 so that the collimator 120 may be attached to a wiper or a bearing wheel that slides along a rail of a cephalometric imaging module (not shown), in a direction orthogonal to the path of an x-ray beam. In one embodiment, the over molded body 114 can form the protrusion 115 using at least two steps. For example, a protrusion is first formed on the overmolded body 114 with a substantially level top surface, and secondly, the protrusion 115 is formed by milling notches 117 in the protrusion to make spaced protrusions 117a. In one embodiment, matching parallel rails mounted on a lower surface of the cephalometric imaging module can support the collimator and the cephalometric sensor. The collimator 120 can then slide along the rail in coincidence with the cephalometric sensor 13 during a scanning process. In one embodiment, the patient positioning unit can be mounted to a rail on the lower surface of the cephalometric imaging module.

Figure 5:
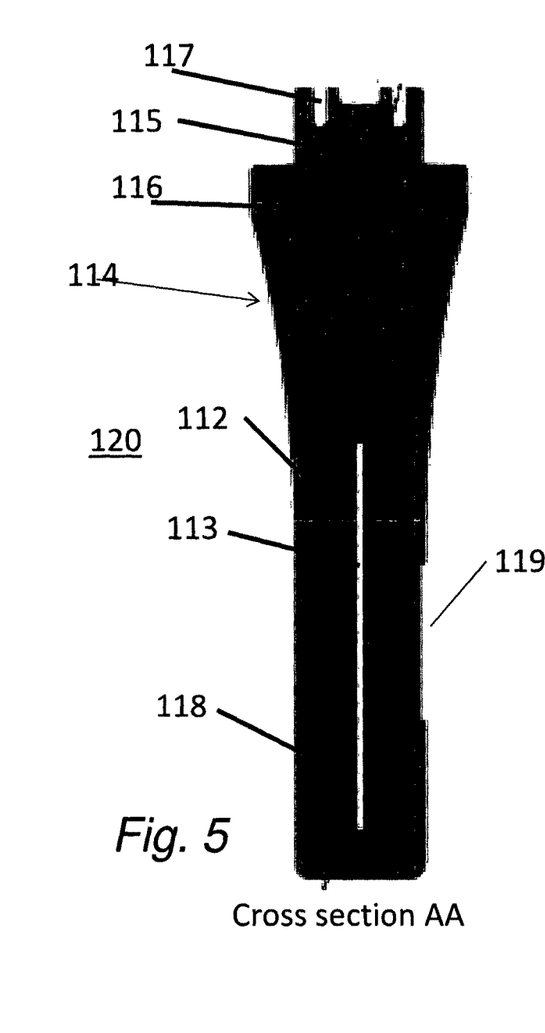
FIG. 5 is a diagram that shows a cross section of the exemplary collimator embodiment of FIG. 3 according to the application along the plane of symmetry parallel to the front face of the collimator.
Figure 6:
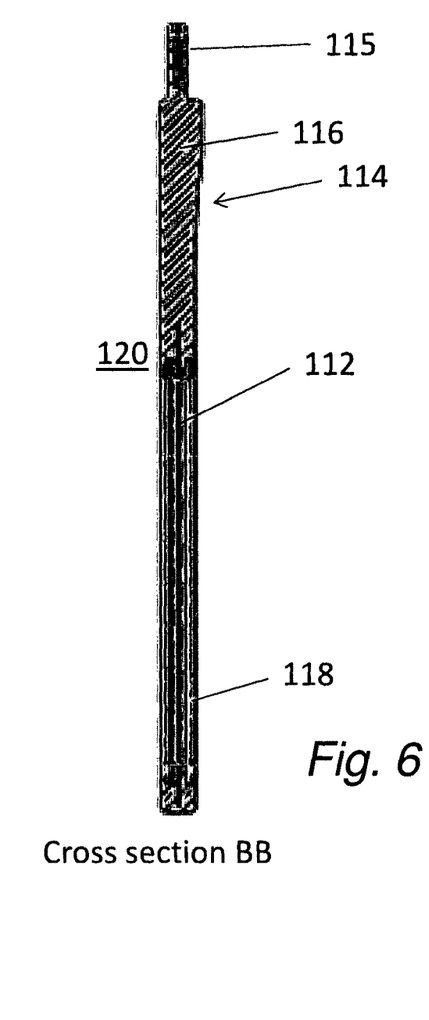
FIG. 6 is a diagram that shows a cross section of the exemplary collimator embodiment of FIG. 3 according to the application along the plane of symmetry crossing the front face of the collimator.

FIG. 5 is a diagram that shows a cross section of the exemplary collimator embodiment of FIG. 3 according to the application along the plane of symmetry parallel to the front face of the collimator. FIG. 6 is a diagram that shows a cross section of the exemplary collimator embodiment of FIG. 3 according to the application along the plane of symmetry crossing the front face of the collimator. As shown in FIG. 6, in certain exemplary embodiments, the width of the protrusion 115 in a direction perpendicular to the front face of the collimator 120 can be comprised between 8 and 25 millimeters, preferably between 11 and 18 mm and more preferably is equal to 14 mm. The lower part 118 of the body 114, namely the part that surrounds the lead plate 112, can have a total thickness comprised between 15 and 21 mm, preferably equal to 18 mm. As the lead plate 112 can have a thickness preferably of 2 mm, the thickness of the layer of FPR material surrounding the lead plate 112 can have a total thickness comprised between 6.5 mm and 9.5 mm, and preferably equal to 8 mm. The intermediate part 116 of the overmolded body 114 that is located between the protrusion 115 and the lead plate 112 can be slightly larger the protrusion 115 and the lower part 118 surrounding the lead plate 112. In one embodiment, the thickness of the intermediate part can be equal to 22 mm. As variously disclosed herein, advantageously the substantially continuous contact between the unitary body 114 and the elongated lead plate 112 is configured to reduce stress forces at a contacting surface therebetween (e.g., orthogonal to the contacting surface).

Figure 7:
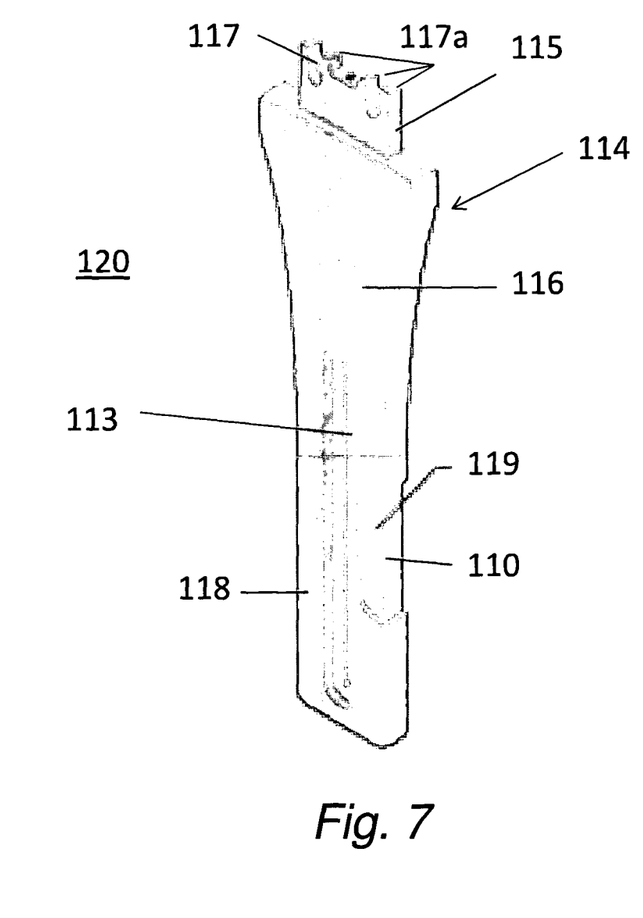
FIG. 7 is a diagram that shows a perspective view of the exemplary collimator embodiment of FIGS. 3-4 according to the application.

Optionally, the body 114 can be overmolded with a recess 119 formed on at least one of the lateral sides (e.g., of the lower body 118). FIG. 7 is a diagram that shows a perspective view of the collimator 120 according to the application. As shown in FIG. 7, the recess 119 can extend around/sideways to a part of the front and rear sides of the body 114. Two molded boss 110 can also be provided in the recess 110 on the front and rear side of the collimator 120. Such an exemplary combination of the recess 119 and boss 110 are selected or intended to detachably snap an additional resilient piece, not represented, that can be for example a visual indicator (e.g., indicator 30) to help the dentist in correctly and/or easily positioning the head of the patient.

Consistent with exemplary embodiments of the application, a computer program utilizes stored instructions that perform on image data that is accessed from an electronic memory. As can be appreciated by those skilled in the image processing arts, a computer program for operating the imaging system in an exemplary embodiment of the present application can be utilized by a suitable, general-purpose computer system, such as a personal computer or workstation. However, many other types of computer systems can be used to execute the computer program of the present application, including an arrangement of networked processors, for example. The computer program for performing exemplary methods/apparatus of the present application may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing exemplary methods/apparatus of the present application may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present application may make use of various image manipulation algorithms and processes that are well known. It will be further understood that the computer program product embodiment of the present application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present application, are not specifically shown or described herein and may be selected from such algorithms, systems, hardware, components and elements known in the art.

In certain exemplary embodiments, the first patient positioning and holding system 6 can include a substantially transparent shield suspended from the mount 2 or the rotatable gantry 3, and a chin positioning element that can include a chin rest and a bite element. In one embodiment, the shield can include an open window disposed between a chin support and a forehead support. In one embodiment, the shield can be visibly transparent, transparent to additional radiation including x-rays and/or formed from a molded polycarbonate material. In one embodiment, the chin support can include a height adjuster for the bite element and the forehead support is configured to be adjustably pivotable toward the patient. In one embodiment, the shield can include one or more controls for setting a column height adjustment for the mount on the shield or mounted on a separate panel that is coupled to the shield. In one embodiment, the shield can include one or more markings to assist in patient positioning. In one embodiment, the shield can include a first Frankfort plane positioning indicator.

In certain exemplary embodiments, an extra-oral imaging system can include a support base adjustable in at least one dimension; a first mount mounted to the support base and configured to revolve an x-ray source and an imaging sensor panel about an imaging area; and a first patient positioning unit coupled to the extra-oral imaging system and positioned between the x-ray source and first sensor so that x-rays impinge the first sensor after radiating the imaging area, including a chin support coupled to the first patient positioning unit and includes a chin positioning element; a head support coupled to the first patient positioning unit shield; and a first Frankfort plan positioning indicator; a second mount mounted to the support base and configured to position a second imaging sensor panel about a second imaging area; and a second patient positioning unit coupled to the second mount and positioned between the x-ray source and the second sensor so that x-rays impinge the second sensor after radiating a second imaging area including a head support coupled to the second patient positioning unit; and a second Frankfort plane positioning indicator. In one embodiment, the second Frankfort plane positioning indicator is fixedly mounted, detachably mounted, or mounted to move between at least two positions, or rotatably mounted. In one embodiment, the second patient positioning unit is configured to repeatably and accurately position a patient between the x-ray source and the second imaging sensor panel.

The invention has been described in detail, and may have been described with particular reference to an exemplary or presently preferred embodiment, but it will be understood that variations and modifications can be effected within the spirit and scope of the invention. For example, exemplary collimator embodiments disclosed herein use lead as an x-ray blocking body defining an elongated fixed slot aperture; however, other metal materials can be used for the lead plate as known to one skilled in the art. Further, in one embodiment, an upper portion of the engagement portion of the collimator can include at least one additional fastener such as a threaded recess for engagement to the transport mechanism. In addition, exemplary apparatus and/or method embodiments according to the application have been described relative to a combined cephalometric, panoramic and computed tomography dental imaging apparatus, but are intended to be applicable to stand-alone cephalometric imaging apparatus or cephalometric imaging apparatus with any additional mode(s) of operation or functionality. The presently disclosed exemplary embodiments are therefore considered in all respects to be illustrative and not restrictive. The scope of the invention is indicated by the appended claims, and all changes that come within the meaning and range of equivalents thereof are intended to be embraced therein.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

The invention claimed is:

1. An extra-oral imaging system, the extra-oral system comprising:
   a support base adjustable in at least one dimension;
   a cephalometric module coupled to the support base and configured to position a cephalometric imaging sensor about a first imaging area formed with an x-ray source, where x-rays from the x-ray source impinge the cephalometric sensor after radiating the first imaging area;
   a cephalometric patient positioning unit positioned operatively near the first imaging area; and
   an integral cephalometric collimator comprising an elongated metallic plate surrounding a fixed slot aperture and encased on at least a portion of all exterior sides by a unitary body in substantially continuous contact with an outer surface of the elongated metallic plate.

2. The extra-oral imaging system of claim 1, where the unitary body comprises a lower portion surrounding the elongated metallic plate and an upper portion, where the upper portion comprises a longitudinal protrusion configured to engage a transport mechanism for translation in a direction orthogonal to a path of the x-rays.

3. The extra-oral imaging system of claim 2, where the engagement portion comprises at least one recess or a plurality of spaced protrusions for engagement to the transport mechanism.

4. The extra-oral imaging system of claim 3, where the upper portion of the engagement portion comprises at least one threaded recess for engagement to the transport mechanism.

5. The extra-oral imaging system of claim 1, where the substantially continuous contact between the unitary body and the elongated metallic plate is configured to reduce stress forces at a contacting surface therebetween (orthogonal to the contacting surface).

6. The extra-oral imaging system of claim 1, where the unitary body is configured to cover substantially all outer surfaces of the elongated metallic plate.

7. The extra-oral imaging system of claim 1, where the unitary body comprises a mixture of polyester resin and glass fiber or is fiber reinforced plastic.

8. The extra-oral imaging system of claim 1, where the fixed slot has a height to width ratio of at least 30, and the unitary body has a variable thickness.

9. The extra-oral imaging system of claim 1, where the unitary body is overmolded on the metallic plate, and where a second slot is milled or machined on the unitary body in coincidence with the fixed aperture.

10. The extra-oral imaging system of claim 1, where the cephalometric patient positioning unit is between the integral cephalometric collimator and the cephalometric imaging sensor, where the cephalometric patient positioning unit comprises:
    a forehead support, the forehead support is adjustable in at least two dimensions; and
    at least one temporal holding member adjustable in at least one dimension; and
    a retractable cephalometric Frankfort plane positioning indicator, where the retractable cephalometric Frankfort plane positioning indicator is configured to be mounted to one or both sides of the integral cephalometric collimator.

11. The extra-oral imaging system of claim 1, comprising:
    a first mount mounted to the support base and configured to revolve the x-ray source and an imaging sensor about a second imaging area so that x-rays impinge the imaging sensor after radiating the second imaging area; and
    a second patient positioning unit coupled to the extra-oral imaging system and positioned operatively near the second imaging area, comprising:
       an elongated shield comprising handles;
       a chin support coupled to the elongated shield and comprising a chin positioning element; and
       a head support coupled to the elongated shield; and
       a second Frankfort plan positioning indicator.

12. A method for manufacturing a collimator for a cephalometric imaging device comprising:
    forming an elongated metallic plate surrounding a fixed aperture;
    overmolding a unitary body on the elongated metallic plate at least partially filling the fixed aperture; and
    milling a slot in the unitary body in coincidence with the fixed aperture.

* * * * *